United States Patent [19]

Möller

[11] Patent Number: 4,941,709
[45] Date of Patent: Jul. 17, 1990

[54] EXAMINATION CHAIR FOR PLACING A PATIENT IN DESIRED POSITIONS FOR E.G. RADIOLOGICAL EXAMINATION

[76] Inventor: Anders Möller, Kullvägen 1, S-135 53 Tyresö, Sweden

[21] Appl. No.: 368,361
[22] PCT Filed: Nov. 30, 1987
[86] PCT No.: PCT/SE87/00566
  § 371 Date: Jun. 1, 1988
  § 102(e) Date: Jun. 1, 1988
[87] PCT Pub. No.: WO88/04149
  PCT Pub. Date: Jun. 16, 1988

[30] Foreign Application Priority Data
Dec. 1, 1986 [SE] Sweden .................... 8605126

[51] Int. Cl.$^5$ ............................ A47C 1/02
[52] U.S. Cl. .................... 297/325; 297/311
[58] Field of Search .......... 297/325, 329, 369, 313, 297/314, 346, 345; 248/398, 371, 157, 420

[56] References Cited

U.S. PATENT DOCUMENTS

| | | | |
|---|---|---|---|
| 2,770,286 | 11/1956 | Weller | 297/314 |
| 3,999,799 | 12/1976 | Daswick | 297/325 |
| 4,173,372 | 4/1979 | Norris | 297/330 |
| 4,383,714 | 5/1983 | Ishida | 297/325 |
| 4,709,960 | 12/1987 | Launes | 297/329 |

FOREIGN PATENT DOCUMENTS 845606 6/1952 Fed. Rep. of Germany ...... 297/325

Primary Examiner—Peter A. Aschenbrenner
Attorney, Agent, or Firm—Brooks & Kushman

[57] ABSTRACT

An examination chair for placing a patient in desired positions for e.g. radiological examination, especially of the lungs and pleurae, comprises an underframe (10) having an arm (12) which is pivotable in the vertical plane and two parallel arcuate sections (17) which are rigidly interconnected and longitudinally displaceably mounted in holders (16) on opposite sides of the end of said arm (12) facing away from the underframe (10) and can be locked in the adjusted position. The arcuate members (17) carry the seat and back-rest assembly (19, 20, 21) of the chair on their side facing the arc center (0) in a manner such that the center of gravity of a person sitting in the chair will lie slightly in front of and below the arc center (0). By pivoting the arm and longitudinally displacing the arcuate members (17), the patient carried by said seat and back-rest assembly (19, 20, 21) is readily positionable in the desired positions.

7 Claims, 7 Drawing Sheets

EXAMINATION CHAIR FOR PLACING A PATIENT IN DESIRED POSITIONS FOR E.G. RADIOLOGICAL EXAMINATION

The present invention relates to a chair for placing a patient in desired positions for e.g. radiological examination, especially of the lungs and pleurae, comprising a preferably wheel-mounted underframe carrying the seat and back-rest assembly of the chair by means of two parallel, rigidly interconnected circular arc sections which are longitudinally displaceably mounted in holders connected to the underframe and can be locked in the adjusted position.

All too few physicians are aware that the examination routines during pneumonography of old, seriously ill, newly operated etc. patients are time-consuming and difficult both for the patient and for the staff. About 40% of pneumonography patients in a general hospital are over 70 years of age. A patient who cannot stand up by himself—as is usually is the case—is admitted sitting in a wheel chair or bed and is first lifted over to the conventional pneumonography frame to sit on a stool for standard images, i.e. frontal and lateral images. In many cases the patient must then wait until the radiologist has approved the images, and if pleural effusion is suspected, the radiologist often requires special images to supplement the images already taken. Then the patient is transferred, frequently by being lifted, to a different place of examination, perhaps in another room, for examination in the lateral position on an examination table. The disposition is often primitive and varies from one hospital to another. Normally, the patient is positioned on two cushions, one underneath the hip and another cushion underneath the shoulder, thereby to project from the examination table the lowest part of the chest where the fluid collects; in other words, the radiation is horizontal. First one side is examined, and then the patient must be lifted and turned over on his other side and the cushions repositioned. After this laborious examination, the patient is left lying on the table until the examination has been approved by the radiologist. This means that the laboratory in question is blocked so that other patient who are in turn must wait. The lateral positioning procedure is so laborious that those most seriously ill, about $\frac{1}{3}$ of the patients, cannot at all be examined in the lateral position. This unfortunate state of things affects about $\frac{1}{4}$ of all pneumonography patients in the hospital, which must be regarded as highly unsatisfactory.

However, I have now developed a quick and more convenient technique for examining pleural effusion. The technique was published in the American Periodical Radiology in January, 1984, Vol. 150, No. 1, pages 245 –249. The new technique can cope with all categories of patients. The patient rests comfortably in the semi-supine position in a chair, slightly inclined to the right, and in this manner both pleurae are simultaneously visualised upon radiological examination in the conventional lung frame while the standard images are being obtained. The entire procedure now is quick and easy, and the old lateral position is seldom required. However, it is somewhat irrational to have, for example, one chair for pneunomography in the sitting position, and another chair for the semi-supine position, and a third arrangement for the lateral position, and to repeatedly lift ill and heavy patients from one place to another. The above-mentioned example of pleural effusion is one aspect and the one which is most common. However, there are also other aspects in which different positions of the body may be involved in pneumonography, and also outside the field of radiologogy, there is a need for positioning patients in different positions, for example for draining pleural fluid and for ultrasonic pleural examination, transillumination checks, and other medical aspects concerning the lungs.

The present invention has several objects which are more or less related to one another, viz.

to simplify the transport of the patient to and from the radiological laboratory;

to reduce the number of patient lifts in pneumonography;

to enable the radiologist to make routine checks of pleural effusion in pneumonography by means of the new semi-supine projection;

to enable the radiologist to take most of the other special projections which may be needed in pneumonography, but which are not mentioned here;

to rationalise the routines of a pneumonography laboratory;

to reduce waiting times and increase the throughput of patients;

to facilitate the work of pneumonography assistants and attendants;

to simplify the draining of pleural fluid and make it more efficient; and to simplify the ultrasonic diagnosis of pleural changes.

To sum up, it should be possible to transport the patient in the chair to and from a radiological laboratory, to allow him to stay in the chair during the entire examination with all its various projections in a manner which makes it easier both for the patient and for the laboratory staff. This object is achieved in that the holders for the circular arc sections of the chair are affixed adjacent one end of an arm or telescopic means mounted vertically movable on the underframe; that the seat and back-rest assembly is affixed to the circular arc sections by means of parallel elongate members bent at an angle and connected at their opposite ends to said sections adjacent the opposite ends thereof, said members being positioned between the sections and the center point of the arc form of said sections; that said seat comprises a lower part fixedly connected to one leg of said elongate members, and a patient-receiving upper part rotatably mounted on said lower part; and that the back-rest is formed of a plurality of supports displaceably mounted on the other leg of said elongate members.

The seat and back-rest assembly is preferably so mounted in the circular arc sections that the center of gravity of a patient sitting on the seat will be located in front of and below the center point of the circular arc form of the sections.

To achieve maximum manoeuvrability of a patient sitting on a chair designed in this manner, the seat is positioned such and the curvature of the sections is selected such that the patient can be readily repositioned about his center of gravity from the sitting to the semi-supine position. By locating the seat in such a manner that the center gravity of the patient will be slightly in front of and below the center point of the curved sections, two advantages are obtained. In the first place, the patient cannot fall backwards if the sections for some reason should become unlocked, or if the examiner should let go of the back-rest when tilting the chair back-wards. Instead, the chair then raises itself up again in a movement which, besides, can be dampened such that the patient will not be thrown forwards, but will come erect slowly and smoothly. The second advantage is that relatively little force is required for repositioning the patient from the erect to the supine position, and even less force for raising the patient again who will come erect under the action of his own weight because his point of gravity is in front of the center of the tilting radius. In this manner, the head end can be lowered through about 30°–35°, and the rotatable seat has a comfortable sitting height of 450–550 mm. By turning the sitting patient sideways through 90° on the chair, the patient can then be readily tilted into a lateral position in the chair. The other lateral position is obtained by raising the chair, turning the patient in the opposite direction, and again tilting the chair. By this simple procedure of raising the patient so that the upper part of the patient's body gets clear of the back-rest, turning the seat (not the chair) through half a revolution, and then tilting the patient into the other lateral position, one avoids the inconvenience of having to turn a supine patient from one side to the other and simultaneously adjusting the patient's position in the field of the X-rays. Naturally, any desired intermediate position or degree of turn therebetween is readily obtainable. This means that the chair can be used also in other applications, primarily medical applications, where it is desired to conveniently posture a person in the positions described above. With this solution, the patient and the chair take up a minimum of space in the laboratory, which is a further advantage in the context.

The invention will be described in more detail below, reference being had to the accompanying drawings illustrating embodiments.

FIG. 6 illustrates more schematically the chair according to the invention with the back-rest tilted to a position below the horizontal plane.

Figure 1:
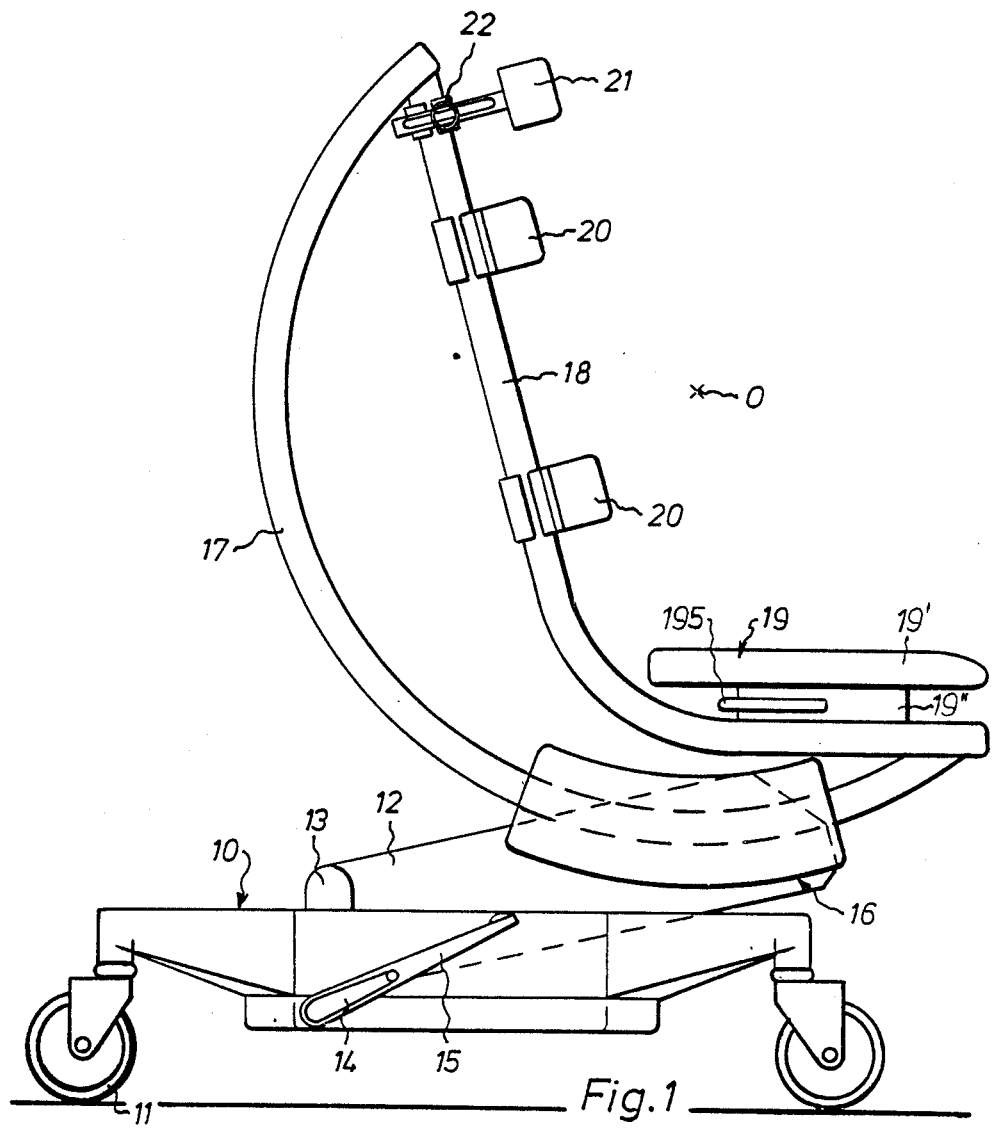
FIG. 1 is a lateral view of the chair according to the invention.

The chair according to the invention as shown in FIG. 1 comprises an underframe 10 which, in the embodiment illustrated, has a central supporting part and projecting arms with wheels 11 at their free ends. Naturally, the underframe 10 may be designed in any manner suitable for the purpose at issue. An arm 12 is vertically and pivotally mounted at 13 on the underframe 10. Instead of this arm, use can be made of a telescoping column. The underframe also has pedals 14 and 15 for operating various details, as will be explained below. At the end of the arm 12 facing away from the underframe 10, holders generally designated 16 are mounted on the opposite sides of the arm 12. Each holder carries a longitudinally displaceable circular arc section 17. The two sections 17 extend parallel to one another and are connected at their opposite ends to two tubular members 18 which also extend parallel with one another and are bent at an angle slightly greater than 90°. The sections and tubular members may be interconnected at their ends by cross-ties 60 (FIG. 8a), and here also a pair of handles for pushing the chair may be mounted. The lower one of the legs obtained by the bending of the tubular members 18 is slightly shorter than the other and carries a seat 19 optionally provided with a foot-rest, while the longer leg carries back-rest members 20 which are preferably displaceable along the two members 18 and can be locked in the adjusted position. Instead of two sections 17 and two members 18, only one of each may be used, in which case the cross-sectional dimensions must normally be slightly increased. The seat 19 comprises two parts, i.e. a lower part 19" fixally connected with the tubular members 18, and an upper part 19' rotatably mounted on the lower part. The back-rest members 20 which are mounted in the desired number, usually two or three, are radiolucent and may be straight or slightly curved. All or some of them may be covered with some type of band which can be made to slide in the longitudinal direction of the back-rest members, i.e. at right angles to the upper part of the body of the sitting patient. This lateral movement of the back-rest members may be synchronised with the turning of the seat so that a supine patient can be turned round from one lateral position to the other. Turning may be effected manually or by means of a motor. At the upper end of the two tubular members, a head-rest 21 is mounted which also is radiolucent and provided with means 22 for adjustment. Like the back-rest members, the head-rest 21 may be in the form two parts separable from one another. The tubular members 18 and the associated seat and back-rest members are located so far on the inner side of the center point 0 of the arc of the sections 17 that the center of gravity of a person sitting in the chair will be in such a position above the seat (about 25 cm) and in front of and below the point 0 (about 5 cm) that the person can be readily turned about the point 0 by displacement of the sections 17 in their holders 16 and then locking the sections in the adjusted position.

Figure 2:
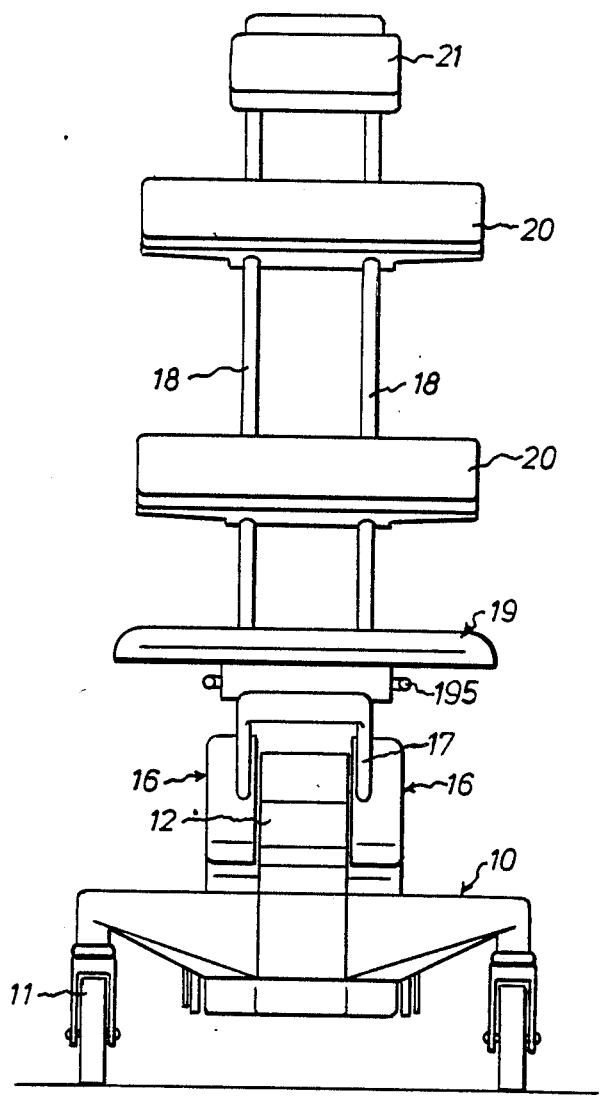
FIG. 2 shows the chair as seen from in front.
Figure 3:
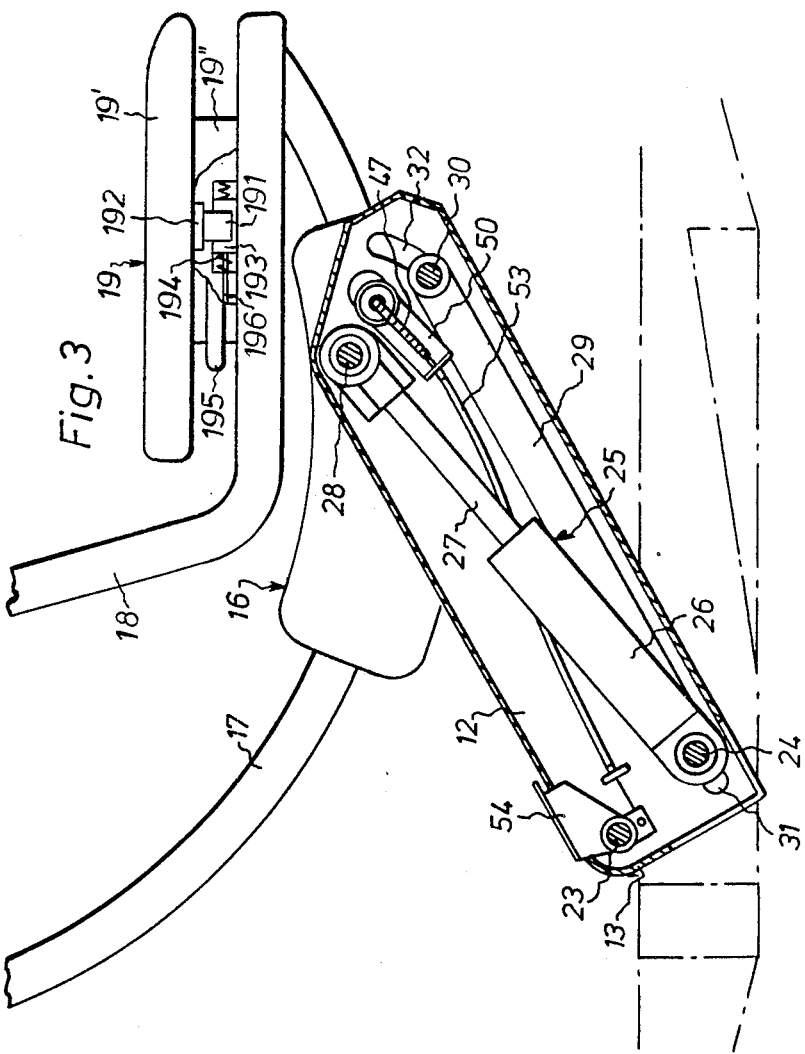
FIG. 3 is a lateral view of an arm mounted on the chair and carrying the seat and back-rest assembly of the chair.

FIG. 3 is an example of the design of the seat 19 and the arm 12. The rotatable upper part 19' of the seat 19 has a pin 191 projecting into the lower part 10" and is mounted in suitable bearings indicated schematically at 192. It is important that the seat can be braked or locked in the adjusted position, and for this reason a braking device is provided which also is shown schematically and which consists of two brake shoes 193 held in engagement with the periphery of the pin 191 by springs 194. To disengage the brake shoes 193 from the pin 191, an operating device 195 in the form of a circular arc yoke 195 is mounted on the outer side of the lower part 19" by means of bearing means (not shown). The yoke 195 is connected, via a suitable transmission 196, to the brake shoes, the arrangement being such that, to achieve disengagement, the yoke 195 is pressed in, reengagement being established when the yoke is released. As will appear from FIGS. 1 and 2, the yoke extends around approximately half the rear periphery of the lower part 19" of the seat. It will be appreciated that many other conventional devices can be used for mounting and locking the upper part 19' in the lower part of the seat. The arm 12 here is in the form of a box section pivotally mounted at 13 by means of a transverse shaft 23. In the transverse direction of the arm and spaced from the shaft 23, a journal 24 is mounted on the underframe 10 and projects into the arm via an arcuate slot 31. A piston and cylinder unit 25 comprises a cylinder 26 pivotally mounted on said journal 24, and a piston 27 pivotally mounted on a journal 28 by which the holders 16 are pivotally connected with the upper end of the arm. Also connected with said holders 16 is a journal 30 extending into the arm 12 via an arcuate slot 32. A rod 29 is pivotally connected at its opposite ends to said journals 24 and 30. When the arm 12 is swung, the piston and cylinder unit 25 is activated, preferably by means of the pedal 15 which is connected to a hydraulic pump (not shown) which, upon such actuation, supplies pressure medium to said piston and cylinder unit. When the arm 12 is swung by means of the piston and the cylinder unit 25, the rod 29 rigidly interconnects the underframe 10 and the holders 16, thereby maintaining said holders in the correct position, regardless of the inclination of the arm 12. The means for swinging the arm 12 and maintaining the holders 16 in correct position are previously known in an per se and may be replaced by other means.

Figure 4:
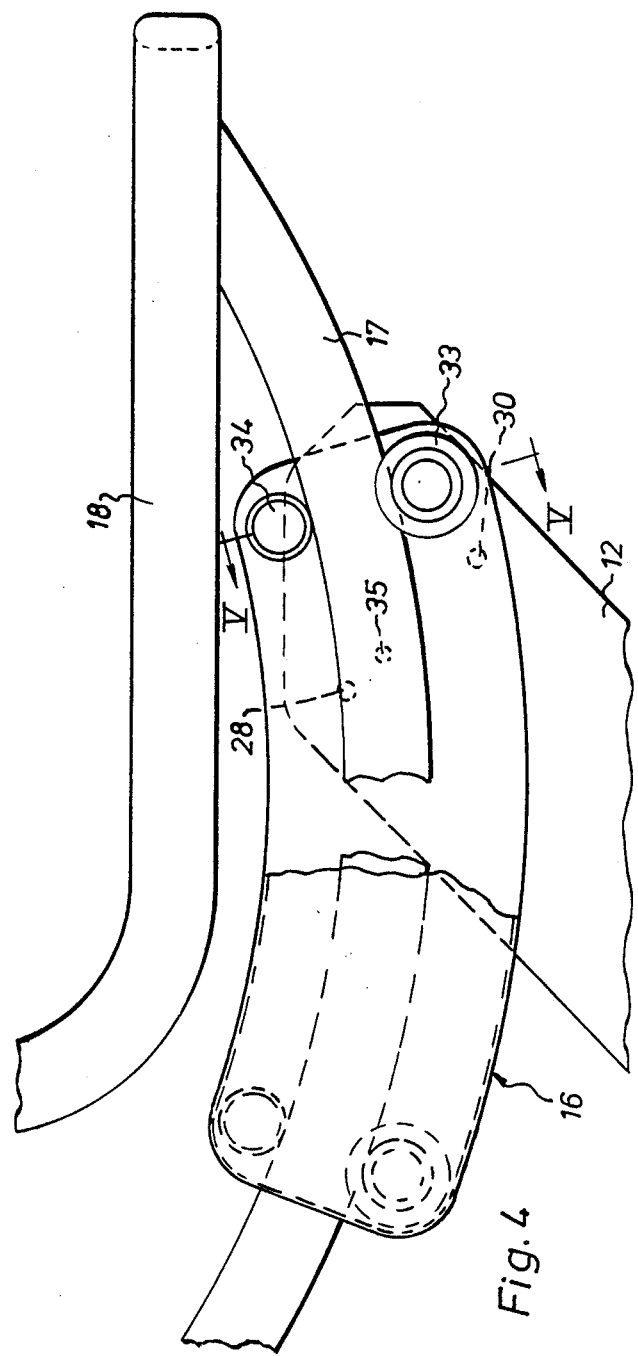
FIG. 4 is a lateral view on a larger scale of a holder for supporting the components which in turn carry the seat and back-rest assembly.
Figure 5:
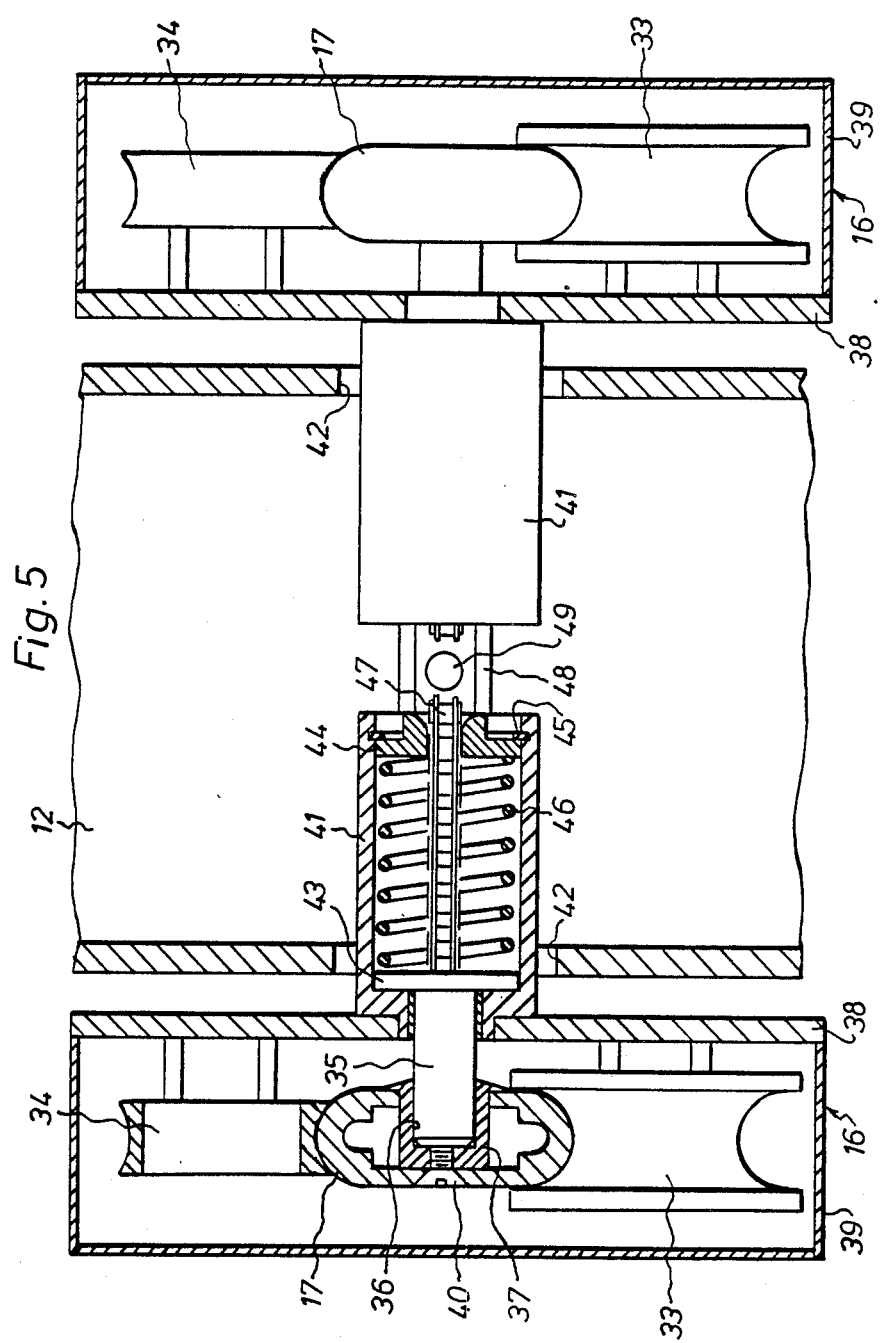
FIGS. 5 and 6 are sections on an even larger scale along line V—V in FIG. 1 and line VI—VI in FIG. 5, respectively.
Figure 6:
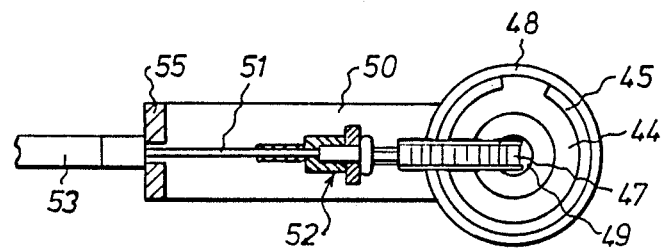

FIGS. 4 and 5 show how the arcuate sections 17 are longitudinally displaceably mounted in their holders 16. In FIG. 5, the sections 17 have a cross-section resembling that of a square tube, with semi-circular upper and lower sides. It will be obvious, however, that they may be either circular or rectangular in cross-section, or may consist of curved rails of different cross-sectional shape. To guide the sections 17 in the holders 16, the holders are provided at their opposed lower corners with rollers 33 having a peripheral groove corresponding to the downwardly facing semi-circular side of the sections 17. To maintain the sections in engagement with the rollers 33, rollers 34 are provided for engaging the upwardly facing side of the sections 17. The rollers 34 have a concave peripheral groove, and the rollers 33 and 34 may be manufactured of plastic material or metal with a suitable coating, and are fixed in a manner not shown in detail to the inner wall 38 on the holders 16 by means of journals. To be able to support the rollers 33, 34, the inner wall 38 of the holders 16 is relatively thick, while the remaining walls of the holders 16 are thinner, as shown in FIG. 5. Thus, the sections 17 can be manually displaced in their longitudinally direction between the pairs of rollers 33, 34, and for locking the sections 17 and thus the seat and back-rest unit 18-21 in the desired position, use may be made of the locking arrangement shown in FIG. 5, in which each section has a locking pin 35 insertable in holes 36 spaced apart at desired intervals in the inner side of the section 17, each hole being formed with a bush 37 provided in a bore in the inner side of the section and held in position by means of a screw 40. For operating the locking pin 35, an opening is provided in the wall 38 of the holder 16, through which opening the locking pin extends and in which also a sleeve 41 is mounted coaxially with the pin 35. In its end wall facing the holder 16, a sleeve 41 has a through bore widening into a larger space within the part of the sleeve 41 facing away from the holder. The locking pin 35 extends through the bore 41 of the sleeve and has in the wider space of said bore a flange 43 which, when the pin 35 is fully extended, engages the shoulder formed between the through opening of the sleeve and the said space. The sleeve 41 extends through a through bore 42 in the arm 12 and terminates at a distance from the longitudinal centerline of the arm. In the end of the sleeve 41 facing away from the holder 16, a washer 44 is inserted which is maintained in position by a locking ring 45. Between the washer 44 and the flange 43 of the locking pin 35, a compression spring 46 is arranged which normally holds the pin 35 in the extended locking position shown in FIG. 5. For displacement of the sections 17 in their holders 16, the locking pins 35 must be retracted, and this is done by means of a chain 47 connected to the flange 43 of the locking pin 35 and extending through a central opening in the washer 44. As will appear from FIG. 5, the sleeves 41 of the holders 16 terminate at a distance from the longitudinal centerline of the arm 12 and are there connected to a short tubular member 48 having midway between its ends an opening 49, through which the chains 47 connected with the opposing locking pins 35 extend to the outer side of the tubular member 48. On the outer side of the tubular member 48, a radially oriented tubular member 50 is secured coaxially with the opening 49. In its end facing away from the tubular member 48, the tubular member 50 has an end wall 55 with a through hole. The chains 47 extending through the opening 49 are connected to a rope or wire 51 by means of a connector 52 provided with tensioning means, said rope or wire 51 extending through the opening in the end wall 55 and along the arm up to an operating member 54 shown in FIG. 3. Between the operating member 54 and the end wall 55, the rope or wire is surrounded by a protective sleeve 53. The operating member 54 is mounted on the journal 23 of the arm and has an actuating portion extending through the arm wall, as shown in FIG. 3. At an angle to said protective portion, the operating member 54 has an angled portion connected to the rope or wire 51. Under the action of the springs 46, the operating member 54 is maintained in swung-out position counterclockwise, and if said member is actuated in the clockwise direction, in accordance with FIG. 3, the rope or wire 51 is tensioned, whereby the springs 46 are compressed and the locking pins 35 are withdrawn from their openings 36 to permit displacement of the sections.

The arrangement of the locking pins 35 implies that the seat and back-rest units of the chair are adjustable stepwise, which may be advantageous in those cases where the radiographic examination requires a patient to be inclined in but a few different and well-defined positions in the chair, but if this is not the case, and if it is necessary to adjust the inclination of the seat and back-rest assembly in a large number of different positions, the locking pin arrangement is replaced by a different locking device comprising, for example, brake shoes which are urged against opposite sides of the sections 17.

As has been mentioned before, the arm 12 is pivoted by means of a hydraulic pump operable by the pedal 15, and for locking the sections 17 in the holders 16 use is made of the member 54 for operating the rope or wire 51 which, however, may also be connected to the pedal 14 shown in FIG. 1. In other words, the chair is operated manually, but it will be appreciated that it can also be equipped with electrical or electrically operated control devices such that the different movements can be initiated and stopped for example by means of press button on a control panel mounted for example on top of the sections 17 or, by means of a bar, on the underframe 10.

Figure 7:
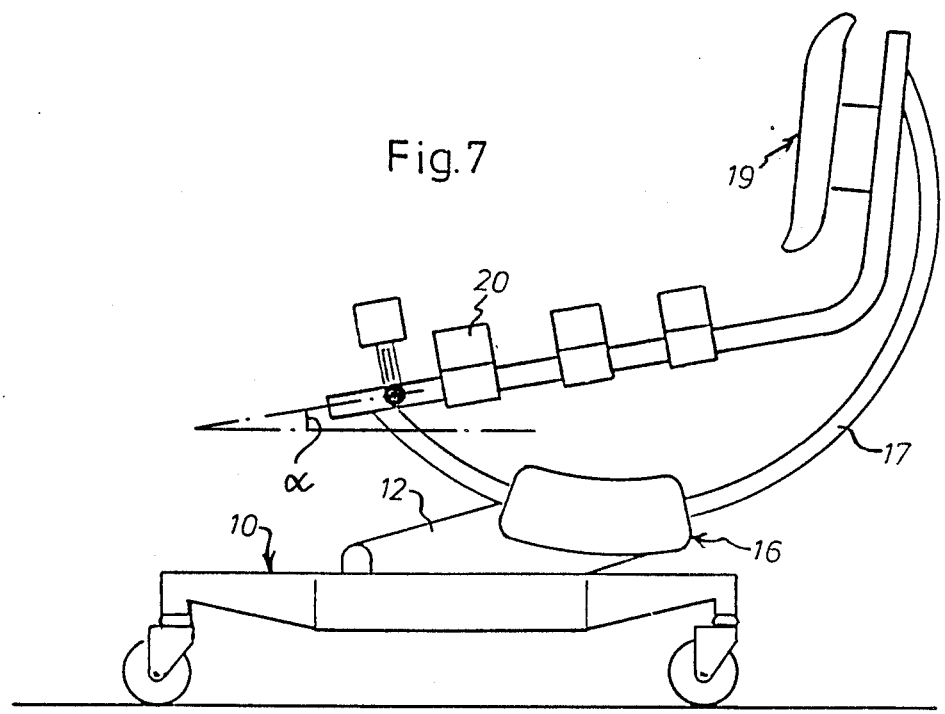

FIG. 7 shows the chair in one of its extreme positions in which the back-rest is inclined so far backwards that it lies below the horizontal plane. The angle of inclination $\alpha$ through which the back-rest can be swung below the horizontal plane amounts maximally to about 30°-35°, which is especially advantageous in the identification of pleural effusion. For such an angle of inclination, the patient is preferably strapped to the seat 19 and, if necessary, to the back-rest members 20 by means of straps (not shown).

Figure 8A:
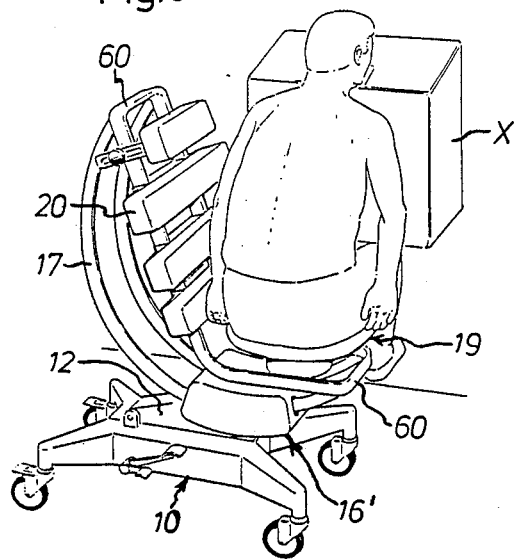
FIGS. 8a–8c are perspective views of the chair during radiography.
Figure 8B:
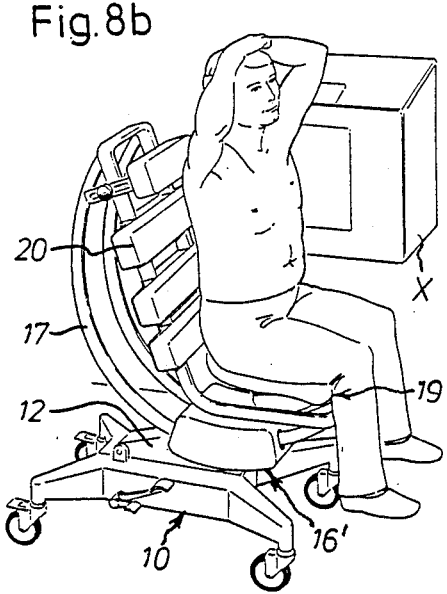
Figure 8C:
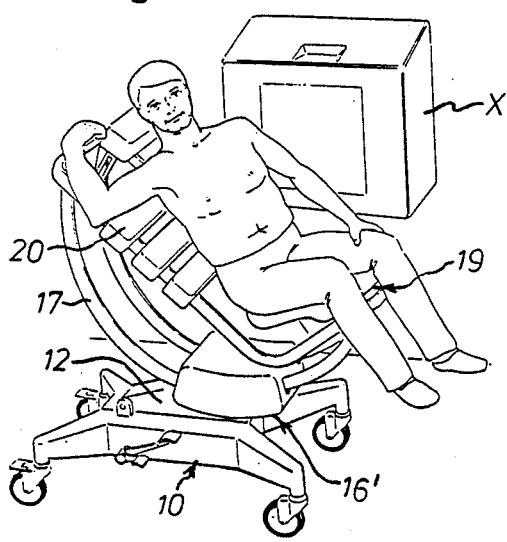

FIGS. 8a-8c illustrate how the chair according to the invention is used for X-ray examination. Thus, the chair can be readily pushed up to and parked in front of an X-ray machine X, and by rotating and, if necessary, raising the seat, the patient can be conveniently and correctly positioned with his chest against the machine (FIG. 8a). By rotating the seat 19, images are then obtainable from the side (FIG. 8b), and by moving the sections 17 in their holders 16 which here are shown to be covered by a cover 16', the seat and the back-rest can be correctly positioned for any special examination.

As has been mentioned above, the chair movements can be controlled manually or by means of motors. If the circular arc sections 17 are to be moved by means of a motor, they are provided on their outer side with a cogged belt meshing with a motor-driven gear.

Especially in the rearwardly inclined positions of the seat and back-rest assembly, it may be necessary to support the patient's legs, and to this end the chair has a leg support (not shown) which is conveniently mounted in connection with the seat 19, for example on one or both of the tubular members 18, or on the lower part 19'' of the seat 19, such that the patient can sit comfortably in all positions. The leg support preferably has a lateral support and comprises a suitable joint, for example a universal joint, so that the leg support can be adjusted in every desired position.

It will be appreciated that all of the positions mentioned in the introduction are obtainable, and that there is no difficulty in repositioning also an old patient who is in pain or otherwise weakened, from the erect to the supine position, without making the patient's sitting position less comfortable, or in turning the patient without lifting, with the patient still in the same relaxed sitting position, or in adjusting the patient to the correct position in, for example, the X-ray beam by means of the wheels and the vertical adjustment function of the chair, or in making the upper part of the patient s body readily accessible from all sides to, for example, an ultrasonic apparatus or a puncture needle.

I claim:

1. Examination chair for placing a patient in desired positions for e.g. radiological examination, especially of the lungs and pleurae, comprising an underframe (10) carrying the seat and back-rest assembly (18, 19, 20, 21) of the chair by means of two parallel, rigidly interconnected circular arc sections (17) which are longitudinally displaceably mounted in holders (16) connected to the underframe and can be locked in the adjusted position characterised in that said holders (16) are affixed adjacent means (12) mounted vertically movable on the underframe (10); that the seat and back-rest assembly (18, 19, 20, 21) is affixed to the circular arc sections (17) by means of parallel elongate members (18) bent at an angle and connected at their opposite ends to said sections adjacent the opposite ends thereof, said members being positioned between the sections and the center point (0) of the arc form of said sections; that said seat (19) comprises a lower part (19'') fixedly connected to one leg of said elongate members (18), and a patient-receiving upper part (19') rotatably mounted on said lower part so that the upper part (19') is rotatable relative to the arc sections (17); and that the back-rest is formed of a plurality of supports displaceably mounted on the other leg of said elongate members (18).

2. A chair as claimed in claim 1, characterised in that said seat and back-rest assembly (18, 19, 20, 21) is so mounted in the circular arc sections (17) that the center of gravity of a patient sitting on the seat will be in front of and below the center point (0) of the circular arc shape of said sections.

3. A chair as claimed in claim 1 or 2, characterised in that the arcuate sections (17) are tubes, especially square tubes, and have an arc length of about 180°.

4. A chair as claimed in claims 1, 2 or 3, characterised in that said vertically movable means (12) is pivotally mounted (13, 23) at one end of the underframe and pivotally carries the holders (16) at its other end, said holders being maintained in position regardless of the inclination of the vertically movable means (12) by means of a rod (29) connected to a journal (24) on the underframe at a distance from the point of pivotment (13, 23) of said vertically movable means (12), and with a journal (30) of said holders (16) at a distance from the pivot point (28) thereof on said vertically movable means (12), said journals (24, 30) extending through arcuate recesses (31, 32) in the vertically movable means (12).

5. A chair as claimed in claim 4, characterised in that a piston and cylinder unit (25) is connected between the journal (24) of the underframe (10) and the pivot point (28) of the holders (16) on the vertically movable means (12).

6. A chair as claimed in claim 1, characterised in that the sections (17) are longitudinally displaceably supported in said holders (16), each by one set of wheels (33, 34) rolling on the contact surfaces of said sections (17) facing toward and away from said seat and back-rest assembly (18, 19, 20, 21).

7. A chair as claimed in claim 1, characterised in that said vertically movable means (12) has locking pins forming the transversely movable locking means (35) and adapted to engage holes (36) in the arcuate sections (17) for locking said sections in the adjusted position.

* * * * *